United States Patent [19]

Stark

[11] Patent Number: 4,590,213

[45] Date of Patent: May 20, 1986

[54] ANTI-ANXIETY METHOD

[75] Inventor: Paul Stark, Indianapolis, Ind.

[73] Assignee: Eli Lilly and Company, Indianapolis, Ind.

[21] Appl. No.: 483,087

[22] Filed: Apr. 8, 1983

[51] Int. Cl.$^4$ .............................................. A61K 31/135
[52] U.S. Cl. .................................................... 514/653
[58] Field of Search ........................... 424/330; 514/653

[56]  References Cited
U.S. PATENT DOCUMENTS

| | | | |
|---|---|---|---|
| 4,018,895 | 4/1977 | Molloy et al. | 424/330 |
| 4,194,009 | 3/1980 | Molloy et al. | 424/330 |
| 4,313,896 | 2/1982 | Molly et al. | 260/501.18 |
| 4,314,081 | 2/1982 | Molloy et al. | 564/347 |
| 4,329,356 | 5/1982 | Holland | 424/274 |

*Primary Examiner*—Stanley J. Friedman
*Attorney, Agent, or Firm*—Leroy Whitaker; Arthur R. Whale

[57] ABSTRACT

This invention provides for a method of treating anxiety which comprises the administration of fluoxetine or norfluoxetine or pharmaceutically aceptable salts thereof.

9 Claims, No Drawings

ANTI-ANXIETY METHOD

BACKGROUND OF THE INVENTION

Fluoxetine[N-methyl-3-(4-trifluoromethylphenoxy)-3-phenylpropylamine]hydrochloride is being examined clinically as an anti-depressant agent in several European countries and the United States. The compound, as taught in U.S. Pat. Nos. 4,018,895 and 4,314,081, has been found to block the uptake of various physiologically active monoamines, especially serotonin. This relatively selective biological action is believed to account for the anti-depressant effect. In addition, it was postulated that this biological action may also be useful in treating disorders of sleep, sexual performance, appetite, muscular function, pituitary function, schizophrenia, and hypothermia. Fluoxetine is particularly desirable as an anti-depressant agent because, unlike most anti-depressants, it is not a sedative.

Norfluoxetine[3-(4-trifluoromethylphenoxy)-3-phenylpropylamine ] is a metabolite of fluoxetine and is also known to block monoamine uptake, especially serotonin. See U.S. Pat. No. 4,313,896.

Most non-sedatory anti-depressant agents are not effective in treating anxiety. Thus, often when treating depression and anxiety, such agents are used in combination with an anti-anxiety agent. Some other anti-depressant agents are also useful in treating anxiety. However, presently used anti-depressant/anti-anxiety agents are also sedatives. It is therefore desirable to discover an anti-anxiety agent which does not cause sedation but which can also be used in the treatment of depression if so indicated.

SUMMARY OF THE INVENTION

This invention provides a method of treating anxiety in a human subject in need of such treatment which comprises the administration of an effective amount of fluoxetine or norfluoxetine or pharmaceutically acceptable salts thereof.

DESCRIPTION OF THE INVENTION

I have discovered that the administration of fluoxetine or norfluoxetine to human patients suffering from anxiety is useful in reducing their anxiety. This effect was entirely unexpected because the compounds are not known to possess any sedative activity. This activity was demonstrated by the following clinical investigation.

In one study, a single investigator performed a randomized, double-blind study comparing fluoxetine, imipramine, and placebo. The 46 test subjects received a daily dose of 20-80 mg. of fluoxetine hydrochloride (median dose 60-80 mg.) in two divided doses, the positive control group of 42 subjects received a daily dose of 100-300 mg. of imipramine hydrochloride (median dose 200-250 mg.) in three divided doses, and the negative control group of 52 subjects received an equal number of placebo capsules administered three times per day. Therapy was continued for up to six weeks. Each subject was evaluated weekly. The end point evaluation was compared to the pre-treatment baseline anxiety evaluation for each subject and then for each group of subjects. Each subject was evaluated on two different scales. On the Covi anxiety scale, both fluoxetine and imipramine were significantly better than placebo in reducing anxiety ($p<0.001$). Surprisingly, this same comparison between fluoxetine and imipramine showed fluoxetine significantly better than imipramine in reducing anxiety ($p=0.005$). The same subjects were evaluated on the anxiety component of the Hamilton depression scale. Once again, as compared to placebo, both fluoxetine ($p<0.001$) and imipramine ($p=0.010$) were significantly more effective in reducing anxiety. As before, fluoxetine was significantly superior to imipramine in reducing anxiety ($p<0.001$).

The preparation of fluoxetine is taught in U.S. Pat. No. 4,314,081. Pharmaceutical compositions containing fluoxetine are claimed in U.S. Pat. No. 4,194,009. The preparation of norfluoxetine, salts, and pharmaceutical formulations are described in U.S. Pat. No. 4,313,896. As used in this invention, it is preferred that the compounds be administered in the form of a pharmaceutically acceptable acid addition salt, especially the hydrochloride salt. It is also preferred that the compounds or their salts be administered in the form of a suitable pharmaceutical preparation. Expecially preferred is a pharmaceutical formulation in unit dosage form which can be administered by the oral route.

I claim:

1. A method for treating anxiety in a human subject in need of such treatment which comprises the administration to said human of an effective amount of fluoxetine or norfluoxetine or pharmaceutically acceptable salts thereof.

2. A method according to claim 1 wherein the compound is fluoxetine or a pharmaceutically acceptable salt thereof.

3. A method according to claim 2 in which the compound is administered orally.

4. A method according to claim 3 in which fluoxetine is administered as the hydrochloride salt.

5. A method according to claim 4 in which the daily dosage level is 20-80 mg.

6. A method according to claim 5 in which the daily dosage level is 60-80 mg.

7. A method according to claim 1 wherein the compound is norfluoxetine or a pharmaceutically acceptable salt thereof.

8. A method according to claim 7 in which the compound is administered orally.

9. A method according to claim 8 in which norfluoxetine is administered as the hydrochloride salt.

* * * * *